US009253980B2

(12) United States Patent
Mueller et al.

(10) Patent No.: US 9,253,980 B2
(45) Date of Patent: Feb. 9, 2016

(54) USE OF SUBSTITUTED DITHIINE-TETRACARBOXIMIDES FOR COMBATING PHYTOPATHOGENIC FUNGI

(75) Inventors: Bernd Mueller, Frankenthal (DE); Nadege Boudet, Hemsbach (DE); Jochen Dietz, Karlsruhe (DE); Wassilios Grammenos, Ludwigshafen (DE); Jan Klaas Lohmann, Lambsheim (DE); Richard Riggs, Mannheim (DE); Ian Robert Craig, Ludwigshafen (DE); Jurith Montag, Ludwigshafen (DE); Egon Haden, Speyer (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/111,270

(22) PCT Filed: Apr. 10, 2012

(86) PCT No.: PCT/EP2012/056400
§ 371 (c)(1),
(2), (4) Date: Oct. 11, 2013

(87) PCT Pub. No.: WO2012/139987
PCT Pub. Date: Oct. 18, 2012

(65) Prior Publication Data
US 2014/0031208 A1    Jan. 30, 2014

Related U.S. Application Data

(60) Provisional application No. 61/475,693, filed on Apr. 15, 2011.

(30) Foreign Application Priority Data

Apr. 15, 2011   (EP) .................................. 11162636

(51) Int. Cl.
*A01N 43/36* (2006.01)
*A01N 43/90* (2006.01)

(52) U.S. Cl.
CPC ............... *A01N 43/36* (2013.01); *A01N 43/90* (2013.01)

(58) Field of Classification Search
None
See application file for complete search history.

(56) References Cited

U.S. PATENT DOCUMENTS

| 3,364,229 A | 1/1968 | Draber et al. | |
| 2010/0120884 A1* | 5/2010 | Seitz et al. | 514/411 |
| 2011/0319462 A1 | 12/2011 | Seitz et al. | |
| 2012/0225923 A1* | 9/2012 | Himmler et al. | 514/411 |

FOREIGN PATENT DOCUMENTS

| WO | WO 2010/043319 | 4/2010 |
| WO | WO 2011/029551 | 3/2011 |

OTHER PUBLICATIONS

Gulten, Sirin. "The synthesis and characterization of Solvatochromic Maleimide fused N-Allyl and N-alkyl-substituted 1,4-dithiines and Diels-Alder Reactions with Anthracene" Journal of Heterocyclic Chemistry, 2010, v. 47, pp. 188-193.*
International Preliminary Report on Patentability dated Oct. 15, 2013, prepared in International Application No. PCT/EP2012/056400.
International Search Report dated May 25, 2012, prepared in International Application No. PCT/EP2012/056400.
Draber, Wilfried, "Synthesis of 1,4-dithiins from maleimide derivatives", Chem. Ber., 1967, p. 1559-1570, vol. 100, XP002563348.
Guelten, Sirine, "The synthesis and characterization of solvatochromic maleimide-fused N-alkyl-substituted 1,4-dithiines and Diels-Adler reactions with athracene", Journal of Heterocyclic Chemistry, Jan. 8, 2010, p. 188-193, vol. 47, No. 1, XP002599987.
Valla, Alain, et al., "Atypical oxidation reaction by thionyl chloride. Easy two-step synthesis of N-alkyl-1,4-dithiines", Synthetic Communications, 2006, p. 3591-3597, vol. 36, XP002599895.
Zentz, F., et al., "Synthesis, in vitro antibacterial and antifungal activities of a series of N-alkyl, 1,4-dithiines", Il Farmico, 2005, p. 944-947, vol. 60 XP005151567.

* cited by examiner

*Primary Examiner* — Mina Haghighatian
*Assistant Examiner* — Erin Hirt
(74) *Attorney, Agent, or Firm* — Brinks Gilson & Lione

(57) ABSTRACT

The present invention relates to the use of dithiine-tetracarboximide compounds of formula I as defined in the description, and the N-oxides, and salts thereof for combating harmful fungi and seed coated with at least one such compound. The invention also relates to novel dithiine-tetracarboximides, processes and intermediates for preparing these compounds and also to compositions comprising at least one such compound.

8 Claims, No Drawings

USE OF SUBSTITUTED DITHIINE-TETRACARBOXIMIDES FOR COMBATING PHYTOPATHOGENIC FUNGI

This application is a National Stage application of International Application No. PCT/EP2012/056400, filed Apr. 10, 2012, which claims the benefit of U.S. Provisional Application No. 61/475,693, filed Apr. 15, 2011, the entire contents of which are hereby incorporated herein by reference. This application also claims priority under 35 U.S.C. §119 to European Patent Application No. 11162636.2, filed Apr. 15, 2011, the entire contents of which is hereby incorporated herein by reference.

The present invention relates to the use of substituted dithiine-tetracarboximides and the N-oxides and the salts thereof for combating phytopathogenic fungi, and to seeds coated with at least one such compound. The invention also relates to novel dithiine-tetracarboximides, processes for preparing these compounds and to compositions comprising at least one such compound.

The use of certain substituted dithiine-tetracarboximides for controlling phytopathogenic fungi is known from WO 2010/043319 and 2011/029551.

The compounds according to the present invention differ from those described in the abovemention publications by the specific substituent $R^1$ that is bound to the nitrogen atom of at least one of the imide moieties.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

This object is achieved by the use of certain substituted dithiine-tetracarboximides having good fungicidal activity against phytopathogenic harmful fungi.

Accordingly, the present invention relates to the use of compounds of formula I:

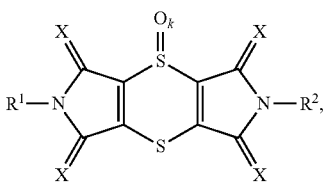

wherein:
X, which may be the same or different to any other X, is O or S;
k indicates the number of the oxygen atoms bound to one sulfur atom of the dithiine moiety and n is 0 or 1;
$R^1$ is $C_2$-$C_6$-alkenyl, $C_2$-$C_6$-alkynyl, —$(CR^CR^D)_n$—Y, —(C=O)—$R^C$ or —O—$R^E$,
  $R^C$, $R^D$ independently of one another are hydrogen, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $NR^AR^B$, $C_3$-$C_6$-cycloalkyl or $C_3$-$C_6$-cycloalkenyl;
  n is an integer and selected from 0, 1, 2 or 3;
  $R^E$, which may be the same or different to any other $R^E$, is hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-cycloalkenyl;
  Y is $NR^AR^B$, CO—$NR^AR^B$, —CN, —$C(R^E)$=N—O—$R^E$ or oxiranyl, $R^A$, $R^B$ independently of one another are hydrogen, cyano, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-alkylcarbonyl, $C_1$-$C_6$-alkenylcarbonyl, $C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl;
$R^2$ is $C_2$-$C_6$-alkenyl, $C_2$-$C_6$-alkynyl, —$(CR^CR^D)_n$—Y, —(C=O)—$R^C$, —O—$R^E$, hydrogen, OH, $C_1$-$C_6$-alkyl, $C_1$-$C_6$-alkoxy-$C_1$-$C_6$-alkyl, $C_3$-$C_6$-cycloalkyl or $C_3$-$C_6$-cycloalkyl-$C_1$-$C_6$-alkyl;
wherein the aliphatic and cyclic groups $R^1$, $R^2$, $R^A$, $R^B$, $R^C$, $R^D$ and/or $R^E$ may carry 1, 2, 3, 4 or up to the maximum possible number of identical or different groups $R^a$ which independently of one another are selected from:
  $R^a$ is halogen, CN, carboxyl, $C_1$-$C_4$-alkyl, $C_1$-$C_4$-haloalkyl, $C_1$-$C_4$-alkoxy, $C_1$-$C_4$-haloalkoxy or $C_3$-$C_6$-cycloalkyl;
and the N-oxides and the agriculturally acceptable salts of the compounds of formula I, and of compositions comprising compounds of formula I, for combating phytopathogenic fungi.

Further, the preparation of certain substituted dithiine-tetracarboximides, inter alia 2,6-diallyl-[1,4]dithiino[2,3-c;5,6-c']dipyrrole-1,3,5,7-tetraone, is mentioned in J. Heterocyclic Chem. (2010), 47, 188-193, U.S. Pat. No. 3,364,229 and Revue Roumaine de Chemie 2005.

The compounds according to the present invention differ from those described in J. Heterocyclic Chem. (2010), 47, 188-193 by the proviso that 2,6-diallyl-[1,4]dithiino[2,3-c;5,6-c']dipyrrole-1,3,5,7-tetraone is being excluded.

Therefore, according to a second aspect, the invention provides compounds of formula I which are represented by formula I having good fungicidal activity against phytopathogenic harmful fungi:

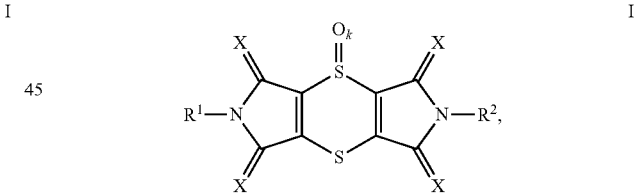

wherein:
X, which may be the same or different to any other X, is O or S;
k indicates the number of the oxygen atoms bound to one sulfur atom of the dithiine moiety and n is 0 or 1;
$R^1$ is $C_2$-$C_6$-alkenyl, $C_2$-$C_6$-alkynyl, —$(CR^CR^D)_n$—Y, —(C=O)—$R^C$ or —O—$R^E$,
  $R^C$, $R^D$ independently of one another are hydrogen, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $NR^AR^B$, $C_3$-$C_6$-cycloalkyl or $C_3$-$C_6$-cycloalkenyl;
  n is an integer and selected from 0, 1, 2 or 3;
  $R^E$, which may be the same or different to any other $R^E$, is hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-cycloalkenyl;
  Y is $NR^AR^B$, CO—$NR^AR^B$, —CN, —$C(R^E)$=N—O—$R^E$ or oxiranyl, $R^A$, $R^B$ independently of one another are hydrogen, cyano, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-alkylcarbonyl, $C_1$-$C_6$-alkenylcarbonyl, $C_1$-$C_6$-alkynylcarbonyl, $C_1$-$C_6$-alkoxycarbonyl, $C_1$-$C_6$-alkenyloxycarbonyl, $C_1$-$C_6$-alkynyloxycarbonyl, $C_1$-$C_6$-alkylaminocarbonyl, di($C_1$-$C_6$-alkyl)aminocarbonyl, $C_1$-$C_6$-alkenylaminocarbonyl or $C_1$-$C_6$-alkynylaminocarbonyl;

$R^2$ is $C_2$-$C_6$-alkenyl, $C_2$-$C_6$-alkynyl, —$(CR^C R^D)_n$—Y, —(C=O)—$R^C$, —O—$R^E$, hydrogen, halogen, OH, $C_1$-$C_6$-alkyl, $C_1$-$C_6$-alkoxy-$C_1$-$C_6$-alkyl, $C_3$-$C_6$-cycloalkyl or $C_3$-$C_6$-cycloalkyl-$C_1$-$C_6$-alkyl;

wherein the aliphatic and cyclic groups $R^1$, $R^2$, $R^A$, $R^B$, $R^C$, $R^D$ and/or $R^E$ may carry 1, 2, 3, 4 or up to the maximum possible number of identical or different groups $R^a$ which independently of one another are selected from:

$R^a$ is halogen, CN, carboxyl, $C_1$-$C_4$-alkyl, $C_1$-$C_4$-haloalkyl, $C_1$-$C_4$-alkoxy, $C_1$-$C_4$-haloalkoxy or $C_3$-$C_6$-cycloalkyl;

except for 2,6-diallyl-[1,4]dithiino[2,3-c;5,6-c']dipyrrole-1,3,5,7-tetraone;

and the N-oxides and the agriculturally acceptable salts of the compounds of formula I.

The term "compounds I" refers to compounds of formula I. Likewise, this terminology applies to all sub-formulae, e.g. "compounds I.2" refers to compounds of formula I.2 or "compounds V" refers to compounds of formula V, etc.

The compounds I can be obtained by various routes in analogy to prior art processes known (cf. U.S. Pat. No. 3,364,229, Synthetic Commun. 36, (2006), 3591-3597, J. Heterocyclic Chem. 47, (2010), 188-193 and II Farmaco 60, (2005), 944-947) and, advantageously, by the synthesis shown in the following schemes and in the experimental part of this application.

In a first process, for example (cf. II Farmaco 60, (2005), 944-947), succinic anhydride II is reacted, in a first step, with an amine III, if appropriate in the presence of a diluent. Thereafter, the resulting succinic monoamides IV are then reacted with a sulfur source (e.g. thionyl chloride). Depending on the reaction conditions, the dithiine-diisoimides V can be isolated before they are converted into compounds I, wherein X is O and k is 0, which are of formula I.A1. If appropriate, the resulting compounds I.A1 can subsequently be oxidized e.g. with nitric acid to form compounds I, wherein k is 1, which are of formula I.A2. The preparation of compounds I can be illustrated by the following scheme (in which R is $R^1$ or $R^2$):

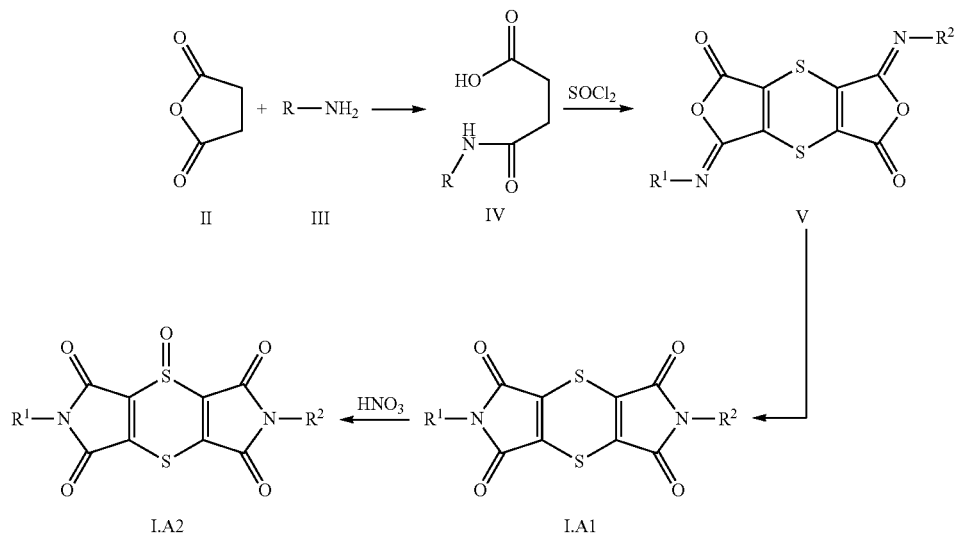

Novel dithiine-diisoimides are those of formula V

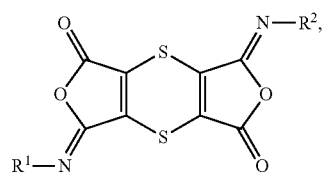

wherein, $R^1$ or $R^2$ have the abovementioned meanings, except 3,7-bis-[(Z)-allylimino]-3H,7H-[1,4]dithiino[2,3-c;5,6-c']difuran-1,5-dione.

In a second process, for example (cf. U.S. Pat. No. 3,364,229, Synthetic Commun. 36, (2006), 3591-3597 and Revue Roumaine de Chimie 50, (2005), 601-607), dichloromaleic anhydride VI is reacted, in a first step, with an amine III, if appropriate in the presence of a diluent. Thereafter, the resulting maleic imides VII are then reacted with a sulfur source (e.g. hydrogen disulfide, sodium or barium trithiocarbanate, sodium sulfide nonahydrate, sodium thiosulfate or thiourea). If appropriate, the resulting dithiine-tetracarboximides I.A1 can subsequently be oxidized with nitric acid. The preparation of the dithiine-tetracarboximides can be illustrated by the following scheme (in which R is $R^1$ or $R^2$):

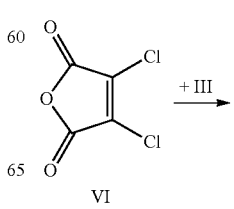

-continued

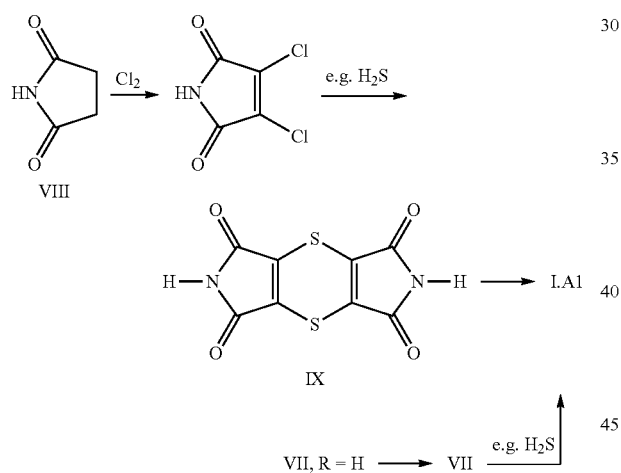

In a third process, for example (cf. U.S. Pat. No. 3,364, 229), dichloromaleimide VII, wherein R is hydrogen, is prepared by photochlorination of succinimide VIII, if appropriate in the presence of UV light and at temperatures between 50 and 250° C. Thereafter, the hydrogen of the NH moiety of the resulting dicholoromaleimide can be readily replaced using standard conditions by R wherein R is $R^1$ or $R^2$ as defined herein to obtain compounds VII. Likewise, the dichloromaleimide may directly be reacted with a sulfur source (e.g. hydrogen disulfide, barium trithiocarbonate or thiourea) to obtain unsubstituted 1,4-dithiin-2,3,5,6-tetracarboxylic acid diimide of formula IX. Thereafter, the hydrogen of both NH moieties of the resulting compound IX can be readily replaced using standard conditions by R wherein R is $R^1$ or $R^2$ as defined herein to obtain compounds I.A1. The preparation of the dithiine-tetracarboximides can be illustrated by the following scheme:

In a fourth process, for example (cf. Chem. Ber. 100, (1967), 1559-1570), compound IX may be reacted at temperatures of from 20° C. to 150° C., preferably in the presence of a base and a diluent, to yield 1,4-dithiine-carboxylic acid compound X. After neutralization with an acid, this compound X is reacted in the presence of an acid and/or a water scavenger, for example with acetanhydride, p-toluene sulfonic acid, sulfuric acid, hydrochloric acid or acetic acid, if appropriate in the presence of a diluent at temperatures of from 20° C. to 150° C. Thereafter, the resulting 1,4-dithiine-tetracarboxylic acid dianhydride XI is then reacted with an amine III to obtain isomeric mixtures of compounds XII. Thereafter, compounds XII can be dehydrated in the presence of an acid and/or a water scavenger, for example with acetanhydride, p-toluene sulfonic acid, sulfuric acid, hydrochloric acid, acetic acid thionylchlorid ohospohorous oxychloride or dicyclohexylcarbodiimide to obtain compounds I.1. The preparation of the dithiine-tetracarboximides can be illustrated by the following scheme:

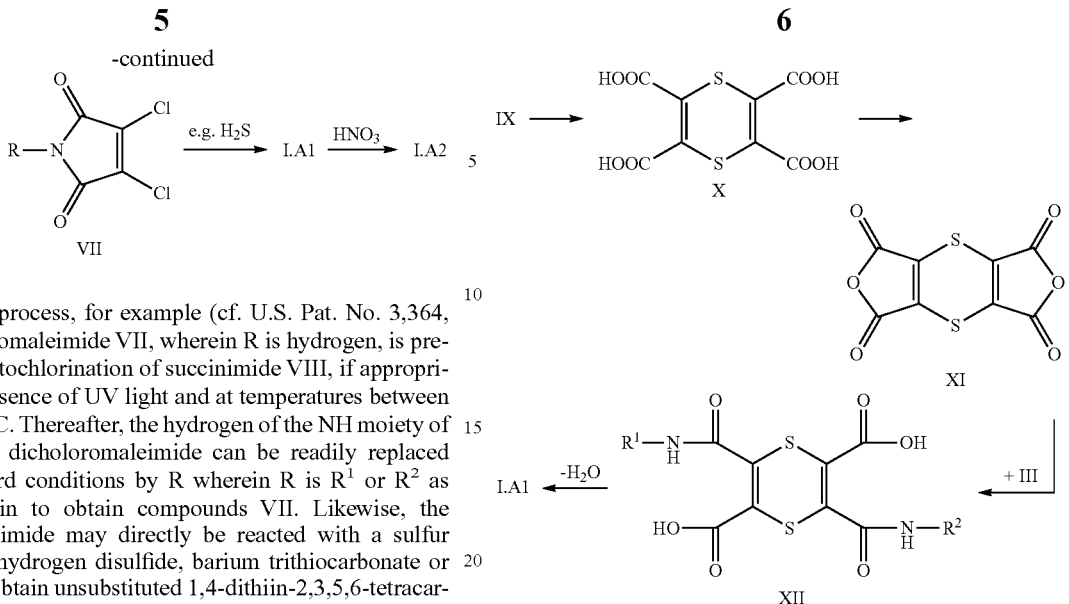

Compounds I, V and XII, wherein $R^1$ is not identical to $R^2$, may be obtained by using intermediates with different R substituents in the respective synthesis steps. Mixtures of such compounds, wherein $R^1$ is not identical to $R^2$, can be used as such, or can be separated, if required.

Compounds I, wherein X is O, which are of formula I.A

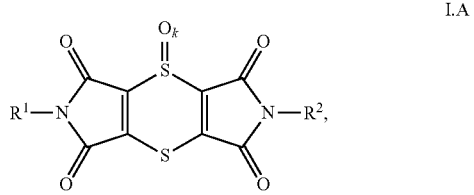

(e.g. compounds I.A1 and I.A2), can be reacted with $P_2S_5$ or Lawesson's Reagent (cf. J. March, Advanced Organic Chemistry, 3. ed, 1985, pp. 793) to obtain compounds I, wherein X is S, which are of formula I.B:

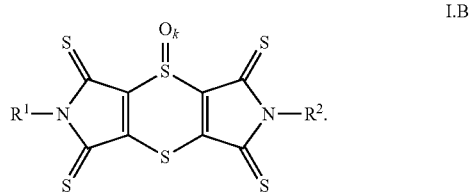

If individual compounds I cannot be obtained by the routes described above, they can be prepared by derivatization of other compounds I.

The N-oxides may be prepared from the compounds I according to conventional oxidation methods, e.g. by treating compounds I with an organic peracid such as meta-chloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e.g. under the action of light, acids or bases). Such conversions may also take place after use, e.g. in the treatment of plants in the treated plant, or in the harmful fungus to be controlled.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_1$-$C_4$-alkyl" refers to a straight-chained or branched alkyl group having 1 to 4 carbon atoms.

The term "$C_1$-$C_6$-alkoxy" refers to a straight-chain or branched alkyl group having 1 to 6 carbon atoms which is bonded via an oxygen, at any position in the alkyl group, e.g. $OCH_3$, $OCH_2CH_3$, $O(CH_2)_2CH_3$, 1-methylethoxy, $O(CH_2)_3CH_3$, 1-methylpropoxy, 2-methylpropoxy or 1,1-dimethylethoxy, $O(CH_2)_4$—$CH_3$ or $O(CH_2)_5CH_3$. Likewise, the term "$C_1$-$C_4$-alkoxy" refers to a straight-chain or branched alkyl group having 1 to 4 carbon atoms which is bonded via an oxygen, at any position in the alkyl group.

The term "$C_1$-$C_4$-alkoxy-$C_1$-$C_4$-alkyl" refers to alkyl having 1 to 4 carbon atoms, wherein one hydrogen atom of the alkyl radical is replaced by a $C_1$-$C_4$-alkoxy group. Likewise, the term "$C_1$-$C_6$-alkoxy-$C_1$-$C_6$-alkyl" refers to alkyl having 1 to 6 carbon atoms, wherein one hydrogen atom of the alkyl radical is replaced by a $C_1$-$C_6$-alkoxy group.

The term "$C_1$-$C_4$-alkylamino" refers to an amino radical carrying one $C_1$-$C_4$-alkyl group as substituent, e.g. methylamino, ethylamino, propylamino, 1-methylethylamino, butylamino, 1-methylpropylamino, 2-methylpropylamino, 1,1-dimethylethylamino and the like. Likewise, the term "$C_1$-$C_6$-alkylamino" refers to an amino radical carrying one $C_1$-$C_6$-alkyl group as substituent.

The term "di($C_1$-$C_4$-alkyl)amino" refers to an amino radical carrying two identical or different $C_1$-$C_4$-alkyl groups as substituents, e.g. dimethylamino, diethylamino, di-n-propylamino, diisopropylamino, N-ethyl-N-methylamino, N-(n-propyl)-N-methylamino, N-(isopropyl)-N methylamino, N-(n-butyl)-N-methylamino, N-(2-butyl)-N methylamino, N-(isobutyl)-N-methylamino, and the like. Likewise, the term "di($C_1$-$C_6$-alkyl)amino" refers to an amino radical carrying two identical or different $C_1$-$C_6$-alkyl groups as substituents.

The term "$C_1$-$C_4$-alkylcarbonyl" refers to a $C_1$-$C_4$-alkyl radical which is attached via a carbonyl group. The term "($C_1$-$C_6$-alkoxy)carbonyl" refers to a $C_1$-$C_6$-alkoxy radical which is attached via a carbonyl group.

The term "$C_1$-$C_6$-alkylaminocarbonyl" refers to a $C_1$-$C_6$-alkylamino radical which is attached via a carbonyl group.

Likewise, the term "di($C_1$-$C_6$-alkyl)aminocarbonyl" refers to a di($C_1$-$C_6$)alkylamino radical which is attached via a carbonyl group.

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, 1-propynyl, 2-propynyl, 1-butynyl, 2-butynyl, 3-butynyl, 1-methyl-2-propynyl. Likewise, the term "$C_2$-$C_6$-alkynyl" refers to a straight-chain or branched unsaturated hydrocarbon radical having 2 to 6 carbon atoms and at least one triple bond.

The term "$C_3$-$C_6$-cycloalkyl" refers to monocyclic, bicyclic, saturated hydrocarbon radicals having 3 to 6 carbon ring members, such as cyclopropyl, cyclobutyl, cyclopentyl or cyclohexyl.

Likewise, the term "$C_3$-$C_6$-cycloalkenyl" refers to unsaturated hydrocarbon radicals having 3 to 6 carbon ring members and a double bond in any position, such as cyclopropenyl, cyclobutenyl, cyclopentenyl or cyclohexenyl.

The term "$C_3$-$C_6$-cycloalkyl-$C_1$-$C_6$-alkyl" refers to alkyl having 1 to 6 carbon atoms (as defined above), wherein one hydrogen atom of the alkyl radical is replaced by a cycloalkyl radical having 3 to 6 carbon atoms (as defined above).

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae provided herein, e.g. formulae I.1 and I.2 and to the intermediates such as compounds II, III, IV and V, wherein the substituents and variables (such as k, n, X, $R^1$, $R^2$, Y, $R^A$, $R^B$, $R^C$, $R^D$, $R^E$, $R^a$ and R) have independently of each other or more preferably in combination the following meanings:

One embodiment of the invention relates to compounds I, wherein X is O, which are of formula I.A.

Another embodiment relates to compounds I, wherein X is S, which are formula I.B.

A further embodiment relates to compounds I, wherein k is 0, which compounds are of formula I.1:

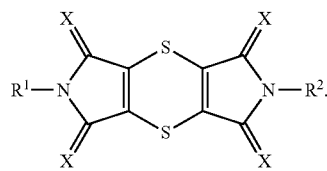

I.1

A more preferred embodiment relates to compounds, wherein k is 0 and X is O, which are of formula I.A1.

A further embodiment relates to compounds I wherein k is 1, which compounds are of formula I.2:

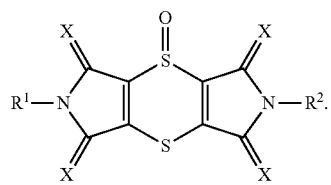

I.2

A more preferred embodiment relates to compounds, wherein k is 1 and X is O, which are of formula I.A2.

In one embodiment of the invention, $R^1$ is selected from $C_2$-$C_6$-alkenyl and $C_2$-$C_6$-alkynyl, more preferably selected from $C_2$-$C_6$-alkenyl, even more preferably from ethenyl, 1-propenyl, 2-propenyl, 3-propenyl, 1-methylethenyl, 1-buten-3-yl, 1-buten-4-yl, 2-buten-1-yl, 3-butenyl, 1-methyl-1-propenyl, 2-methyl-1-propenyl, 1-methyl-2-propenyl and 2-methyl-2-propenyl.

In another embodiment, $R^1$ is $C_2$-$C_6$-alkynyl, preferably selected from propinyl, butinyl, pentinyl, even more preferably propin-3-yl, butin-4-yl, 2-butin-1-yl.

In another embodiment, $R^1$ is $C_2$-$C_6$-alkynyl, —$(CR^CR^D)_n$—Y, —(C=O)—$R^C$ or —O—$R^E$.

In a further embodiment, $R^1$ is —$(CR^CR^D)_n$—Y. In this embodiment, n is preferably 0, 1 or 2, more preferably 0 or 1, in particular n is 1.

Amongst compounds I, wherein $R^1$ is —$(CR^CR^D)_n$—Y, $R^C$ and $R^D$ are preferably selected from hydrogen and $C_1$-$C_6$-alkyl, more preferably from hydrogen and $C_1$-$C_4$-alkyl, even more preferably from methyl and hydrogen.

Amongst compounds I, wherein $R^1$ is —$(CR^CR^D)_n$—Y, preference given to those, wherein Y is $NR^AR^B$, wherein preferably $R^A$ and $R^B$ are selected from hydrogen, cyano, $C_1$-$C_6$-alkylcarbonyl and $C_1$-$C_6$-alkyl, more preferably from hydrogen and $C_1$-$C_4$-alkyl and even more preferably from methyl and hydrogen.

Amongst compounds I, wherein $R^1$ is —$(CR^CR^D)_n$—Y, preference given to those, wherein Y is CO—$NR^AR^B$, wherein preferably $R^A$ and $R^B$ are selected from hydrogen, cyano, $C_1$-$C_6$-alkylcarbonyl and $C_1$-$C_6$-alkyl, more preferably from hydrogen and $C_1$-$C_4$-alkyl and even more preferably from methyl and hydrogen.

Amongst compounds I, wherein $R^1$ is —$(CR^CR^D)_n$—Y, preference is also given to those, wherein Y is —CN.

Amongst compounds I, wherein $R^1$ is —$(CR^CR^D)_n$—Y, preference is also given to those, wherein Y is oxiranyl.

Amongst compounds I, wherein $R^1$ is —$(CR^CR^D)_n$—Y, preference is also given to those, wherein Y is —C($R^E$)=N—O—$R^E$, wherein preferably $R^E$ is selected from hydrogen, $C_1$-$C_6$-alkyl, $C_2$-$C_6$-alkenyl, and $C_3$-$C_6$-cycloalkyl, more preferably from hydrogen and $C_1$-$C_6$-alkyl and even more preferable from methyl and hydrogen.

Amongst compounds I, wherein $R^1$ is —$(CR^CR^D)_n$—Y, preference is also given to those, wherein Y is —CH=N—O—$R^E$, wherein preferably $R^E$ is selected from hydrogen, $C_1$-$C_6$-alkyl, $C_2$-$C_6$-alkenyl, and $C_3$-$C_6$-cycloalkyl, more preferably from hydrogen and $C_1$-$C_6$-alkyl and even more preferable from $C_1$-$C_4$-alkyl.

A further embodiment relates to compounds I, wherein $R^1$ is —(C=O)—$R^C$. Amongst compounds I, wherein $R^1$ is —(C=O)—$R^C$, $R^C$ is preferably selected hydrogen, $C_1$-$C_6$-alkyl, $C_2$-$C_6$-alkenyl, $C_1$-$C_6$-alkoxy, $NR^AR^B$ and $C_3$-$C_6$-cycloalkyl, more preferably from $NR^AR^B$, $C_1$-$C_6$-alkyl and $C_1$-$C_6$-alkoxy, in particular $C_1$-$C_4$-alkyl.

A further embodiment relates to compounds I, wherein $R^1$ is —O—$R^E$. Amongst compounds I, wherein $R^1$ is —O—$R^E$, $R^E$ is preferably selected from hydrogen, $C_1$-$C_6$-alkyl, $C_2$-$C_6$-alkenyl and $C_3$-$C_6$-cycloalkyl, more preferably from hydrogen and $C_1$-$C_6$-alkyl, in particular from $C_1$-$C_4$-alkyl.

All preferred embodiments relating to $R^1$ are likewise also preferred from embodiments concerning the group $R^2$.

A further embodiment relates to compounds I, wherein $R^2$ is identical to $R^1$.

A further embodiment relates to compounds I, wherein $R^2$ is hydrogen or $C_1$-$C_6$-alkyl, more preferably hydrogen, methyl or ethyl, in particular methyl.

A skilled person will readily understand that the preferences given in connection with compounds I apply for formulae I.A1, I.A2, I.B and V as defined above.

With respect to their use, particular preference is given to the compounds of formulae I and I.A1 to I.B2 compiled in the tables 1 to 2 below. Here, the groups mentioned in the Tables for a substituent are furthermore, independently of the combination wherein they are mentioned, a particularly preferred embodiment of the substituent in question.

TABLE 1

Compounds of formula I.A1, wherein X is O and k is 0.

| No. | $R^1$ | $R^2$ |
|---|---|---|
| 1 | —$CH_2$—CH=$CH_2$ | —$CH_2$—CH=$CH_2$ |
| 2 | —$CH_2$—C($CH_3$)=$CH_2$ | —$CH_2$—C($CH_3$)=$CH_2$ |
| 3 | —$CH_2$—$CH_2$—CH=$CH_2$ | —$CH_2$—$CH_2$—CH=$CH_2$ |

TABLE 1-continued

Compounds of formula I.A1, wherein X is O and k is 0.

| No. | R$^1$ | R$^2$ |
|---|---|---|
| 4 | —CH$_2$—CH$_2$=CH$_2$—CH$_3$ | —CH$_2$—CH$_2$=CH$_2$—CH$_3$ |
| 5 | —CH$_2$—CH$_2$=CH$_2$—CH$_2$—OCH$_3$ | —CH$_2$—CH$_2$=CH$_2$—CH$_2$—OCH$_3$ |
| 6 | —CH$_2$—C≡CH | —CH$_2$—C≡CH |
| 7 | —CH$_2$—CH$_2$—C≡CH | —CH$_2$—CH$_2$—C≡CH |
| 8 | —CH$_2$—CH=C—CH$_3$ | —CH$_2$—CH=C—CH$_3$ |
| 9 | —CH$_2$—CH=C—CH—OCH$_3$ | —CH$_2$—CH=C—CH—OCH$_3$ |
| 10 | —NH$_2$ | —NH$_2$ |
| 11 | —NH(CH$_3$) | —NH(CH$_3$) |
| 12 | —N(CH$_3$)$_2$ | —N(CH$_3$)$_2$ |
| 13 | —NH(C$_2$H$_5$) | —NH(C$_2$H$_5$) |
| 14 | —NCH$_3$(C$_2$H$_5$) | —NCH$_3$(C$_2$H$_5$) |
| 15 | —N(C$_2$H$_5$)$_2$ | —N(C$_2$H$_5$)$_2$ |
| 16 | —NH—CHO | —NH—CHO |
| 17 | —N(CH$_3$)—CHO | —N(CH$_3$)—CHO |
| 18 | —NH—CO—CH$_3$ | —NH—CO—CH$_3$ |
| 19 | —N(CH$_3$)—CO—CH$_3$ | —N(CH$_3$)—CO—CH$_3$ |
| 20 | —NH—CO—C$_2$H$_5$ | —NH—CO—C$_2$H$_5$ |
| 21 | —N(CH$_3$)—CO—C$_2$H$_5$ | —N(CH$_3$)—CO—C$_2$H$_5$ |
| 22 | —NH—CO—CF$_3$ | —NH—CO—CF$_3$ |
| 23 | —N(CH$_3$)—CO—CF$_3$ | —N(CH$_3$)—CO—CF$_3$ |
| 24 | —NH—CO—cyclo-C$_3$H$_5$ | —NH—CO—cyclo-C$_3$H$_5$ |
| 25 | —N(CH$_3$)—CO—cyclo-C$_3$H$_5$ | —N(CH$_3$)—CO—cyclo-C$_3$H$_5$ |
| 26 | —NH—CO—CH$_2$—OCH$_3$ | —NH—CO—CH$_2$—OCH$_3$ |
| 27 | —N(CH$_3$)—CO—CH$_2$—OCH$_3$ | —N(CH$_3$)—CO—CH$_2$—OCH$_3$ |
| 28 | —N—CH$_2$—N(CH$_3$)$_2$ | —N—CH$_2$—N(CH$_3$)$_2$ |
| 29 | —NH—(CH$_2$)$_2$—NH$_2$ | —NH—(CH$_2$)$_2$—NH$_2$ |
| 30 | —N(CH$_3$)—(CH$_2$)$_2$—NH$_2$ | —N(CH$_3$)—(CH$_2$)$_2$—NH$_2$ |
| 31 | —NH—(CH$_2$)$_2$—NHCH$_3$ | —NH—(CH$_2$)$_2$—NHCH$_3$ |
| 32 | —N(CH$_3$)—(CH$_2$)$_2$—NHCH$_3$ | —N(CH$_3$)—(CH$_2$)$_2$—NHCH$_3$ |
| 33 | —NH(CH$_2$)$_2$—N(CH$_3$)$_2$ | —NH—(CH$_2$)$_2$—N(CH$_3$)$_2$ |
| 34 | —N(CH$_3$)—(CH$_2$)$_2$—N(CH$_3$)$_2$ | —N(CH$_3$)—(CH$_2$)$_2$—N(CH$_3$)$_2$ |
| 35 | —NH—(CH$_2$)$_2$—NHC$_2$H$_5$ | —NH—(CH$_2$)$_2$—NHC$_2$H$_5$ |
| 36 | —N(CH$_3$)—(CH$_2$)$_2$—NHC$_2$H$_5$ | —N(CH$_3$)—(CH$_2$)$_2$—NHC$_2$H$_5$ |
| 37 | —NH—(CH$_2$)$_2$—N(CH$_3$)C$_2$H$_5$ | —NH—(CH$_2$)$_2$—N(CH$_3$)C$_2$H$_5$ |
| 38 | —N(CH$_3$)—(CH$_2$)$_2$—N(CH$_3$)C$_2$H$_5$ | —N(CH$_3$)—(CH$_2$)$_2$—N(CH$_3$)C$_2$H$_5$ |
| 39 | —NH—(CH$_2$)$_2$—N(C$_2$H$_5$)$_2$ | —NH—(CH$_2$)$_2$—N(C$_2$H$_5$)$_2$ |
| 40 | —N(CH$_3$)—(CH$_2$)$_2$—N(C$_2$H$_5$)$_2$ | —N(CH$_3$)—(CH$_2$)$_2$—N(C$_2$H$_5$)$_2$ |
| 41 | —NH—(CH$_2$)$_2$—NH—CHO | —NH—(CH$_2$)$_2$—NH—CHO |
| 42 | —N(CH$_3$)—(CH$_2$)$_2$—NH—CHO | —N(CH$_3$)—(CH$_2$)$_2$—NH—CHO |
| 43 | —NH—(CH$_2$)$_2$—NH—CO—CH$_3$ | —NH—(CH$_2$)$_2$—NH—CO—CH$_3$ |
| 44 | —N(CH$_3$)—(CH$_2$)$_2$—NH—CO—CH$_3$ | —N(CH$_3$)—(CH$_2$)$_2$—NH—CO—CH$_3$ |
| 45 | —NH—(CH$_2$)$_2$—NH—CO—C$_2$H$_5$ | —NH—(CH$_2$)$_2$—NH—CO—C$_2$H$_5$ |
| 46 | —N(CH$_3$)—(CH$_2$)$_2$—NH—CO—C$_2$H$_5$ | —N(CH$_3$)—(CH$_2$)$_2$—NH—CO—C$_2$H$_5$ |
| 47 | —NH—(CH$_2$)$_2$—NH—CO—CF$_3$ | —NH—(CH$_2$)$_2$—NH—CO—CF$_3$ |
| 48 | —N(CH$_3$)—(CH$_2$)$_2$—NH—CO—CF$_3$ | —N(CH$_3$)—(CH$_2$)$_2$—NH—CO—CF$_3$ |
| 49 | —NH—(CH$_2$)$_2$—NH—CO—cyclo-C$_3$H$_7$ | —NH—(CH$_2$)$_2$—NH—CO—cyclo-C$_3$H$_7$ |
| 50 | —N(CH$_3$)—(CH$_2$)$_2$—NH—CO—cyclo-C$_3$H$_7$ | —N(CH$_3$)—(CH$_2$)$_2$—NH—CO—cyclo-C$_3$H$_7$ |
| 51 | —NH—(CH$_2$)$_2$—NH—CO—CH$_2$—OCH$_3$ | —NH—(CH$_2$)$_2$—NH—CO—CH$_2$—OCH$_3$ |
| 52 | —N(CH$_3$)—(CH$_2$)$_2$—NH—CO—CH$_2$—OCH$_3$ | —N(CH$_3$)—(CH$_2$)$_2$—NH—CO—CH$_2$—OCH$_3$ |
| 53 | —CN | —CN |
| 54 | —CH$_2$—CN | —CH$_2$—CN |
| 55 | —CH(CH$_3$)—CN | —CH(CH$_3$)—CN |
| 56 | —CH$_2$—CH$_2$—CN | —CH$_2$—CH$_2$—CN |
| 57 | —CH=N—OCH$_3$ | —CH=N—OCH$_3$ |
| 58 | —CH=N—OC$_2$H$_5$ | —CH=N—OC$_2$H$_5$ |
| 59 | —C(CH$_3$)=N—OCH$_3$ | —C(CH$_3$)=N—OCH$_3$ |
| 60 | —C(CH$_3$)=N—OC$_2$H$_5$ | —C(CH$_3$)=N—OC$_2$H$_5$ |
| 61 | —CH$_2$—CH=N—OCH$_3$ | —CH$_2$—CH=N—OCH$_3$ |
| 62 | —CH$_2$—CH=N—OC$_2$H$_5$ | —CH$_2$—CH=N—OC$_2$H$_5$ |
| 63 | —CH$_2$—CH=N—O—n-C$_3$H$_7$ | —CH$_2$—CH=N—O—n-C$_3$H$_7$ |
| 64 | —CH$_2$—CH=N—O—i-C$_3$H$_7$ | —CH$_2$—CH=N—O—i-C$_3$H$_7$ |
| 65 | —CH$_2$—C(CH$_3$)=N—OCH$_3$ | —CH$_2$—C(CH$_3$)=N—OCH$_3$ |
| 66 | —CH$_2$—C(CH$_3$)=N—OC$_2$H$_5$ | —CH$_2$—C(CH$_3$)=N—OC$_2$H$_5$ |
| 67 | —CH$_2$—C(CH$_3$)=N—O—n-C$_3$H$_7$ | —CH$_2$—C(CH$_3$)=N—O—n-C$_3$H$_7$ |
| 68 | —CH$_2$—C(CH$_3$)=N—O—i-C$_3$H$_7$ | —CH$_2$—C(CH$_3$)=N—O—i-C$_3$H$_7$ |
| 69 | —CHO | —CHO |
| 70 | —CO—CH$_3$ | —CO—CH$_3$ |
| 71 | —CO—C$_2$H$_5$ | —CO—C$_2$H$_5$ |
| 72 | —CO—n-C$_3$H$_7$ | —CO—n-C$_3$H$_7$ |
| 73 | —CO—i-C$_3$H$_7$ | —CO—i-C$_3$H$_7$ |
| 74 | —CO—OCH$_3$ | —CO—OCH$_3$ |
| 75 | —CO—OC$_2$H$_5$ | —CO—OC2H$_5$ |
| 76 | —CO—O—n-C$_3$H$_7$ | —CO—O—n-C$_3$H$_7$ |
| 77 | —CO—O—i-C$_3$H$_7$ | —CO—O—i-C$_3$H$_7$ |
| 78 | —CO—NH$_2$ | —CO—NH$_2$ |
| 79 | —CO—NH(CH$_3$) | —CO—NH(CH$_3$) |

TABLE 1-continued

Compounds of formula I.A1, wherein X is O and k is 0.

| No. | $R^1$ | $R^2$ |
|---|---|---|
| 80 | —CO—N(CH$_3$)$_2$ | —CO—N(CH$_3$)$_2$ |
| 81 | —CO—NH(C$_2$H$_5$) | —CO—NH(C$_2$H$_5$) |
| 82 | —CO—N(CH$_3$)(C$_2$H$_5$) | —CO—N(CH$_3$)(C$_2$H$_5$) |
| 83 | —CO—N(C$_2$H$_5$)$_2$ | —CO—N(C$_2$H$_5$)$_2$ |
| 84 | OH | OH |
| 85 | —O—CH$_3$ | —O—CH$_3$ |
| 86 | —O—C$_2$H$_5$ | —O—C$_2$H$_5$ |
| 87 | —O—n-C$_3$H$_7$ | —O—n-C$_3$H$_7$ |
| 88 | —O—i-C$_3$H$_7$ | —O—i-C$_3$H$_7$ |
| 89 | —O—n-C$_4$H$_9$ | —O—n-C$_4$H$_9$ |
| 90 | —O—sec-C$_4$H$_9$ | —O—sec-C$_4$H$_9$ |
| 91 | —O—i-C$_4$H$_9$ | —O—i-C$_4$H$_9$ |
| 92 | —O—t-C$_4$H$_9$ | —O—t-C$_4$H$_9$ |

TABLE 2

Compounds of formula I

| No. | $R^1$ | $R^2$ | X | k |
|---|---|---|---|---|
| 1 | —OCH$_3$ | —OCH$_3$ | O | 1 |
| 2 | —OCH$_3$ | —OC$_2$H$_5$ | O | 0 |
| 3 | —CH$_2$—CH═N—OCH$_3$ | —CH$_2$—CH═N—OCH$_3$ | S | 0 |

The entries to column X in table 2 means that all four X substituents in formula I have the same meaning.

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp).

Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

The compounds I and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternate*), tomatoes (e.g. *A. solani* or *A. alternate*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B.

*sorokiniana*) on cereals and e.g. *B. oryzae* on rice and turfs; *Blumena* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorodniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminiCola*: Anthracnose stalk rot), soft fruits, potatoes (e.g. *C. coccodes*: black dot), beans (e.g. *C. lindemuthianum*) and soybeans (e.g. *C. truncatum* or *C. gloeosporiodes*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectna* or *Neonectna* spp.) on fruit trees, vines (e.g. *C. liriodendri*, teleomorph: *Neonectria liriodendri*: Black Foot Disease) and ornamentals; *Dematophora* (teleomorph: *Roselinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitipona* (syn. *Phellinus*) *punctata*, *F. mediterranea*, *Phaeomoniella chlamydospora* (earlier *Phaeo-acremonium chlamydosporum*), *Phaeoacremonium aleophllum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exseroholum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticilliodes* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella angulata* on vines, pome fruits and other plants and *G. gossypii* on cotton; Grain-staining complex on rice; *Guignardia bewellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemilsia* spp., e.g. *H. vastataX* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoia tritici*, *Septoria blotch*) on wheat or *M. figiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphda* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyriculana* spp., e.g. *P. oryzae*(teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycmes* (brown spot) on soybeans, *S. tritici* (*Septoria blotch*) on wheat and S. (syn. *Stagonospora*) *nodorum* (*Stagonospora blotch*) on cereals; *Uncinula* (syn. *Elysiphe*) *necator* (powdery mildew, anamorph: *Odium tuckeri*) on vines; *Setospaeria* spp. (leaf blight) on corn (e.g. *S. turcicum*, syn. *Helminthosporium turcicum*) and turf; *Sphacelotheca* spp.

(smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Tfichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecdomyces* spp. and Zygomycetes such as *Mucor* spp., and in addition in the protection of stored products and harvest the following yeast fungi are worthy of note: *Candida* spp. and *Saccharomyces cerevisae*.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising a solvent or solid carrier and at least one compound I and to the use for controlling harmful fungi.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144, 050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as lignin-soulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C.I. pigment red 112, C.I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds I and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, atta-clay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typcially, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The compositions according to the invention can, in the use form as fungicides, also be present together with other active substances, e.g. with herbicides, insecticides, growth regulators, fungicides or else with fertilizers, as pre-mix or, if appropriate, not until immediately prior to use (tank mix).

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds according to the invention can be used, is intended to illustrate the possible combinations but does not limit them:

A) Respiration inhibitors
Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/ flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl) phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom;

inhibitors of complex II (e.g. carboxamides): benodanil, bixafen, boscalid, carboxin, fenfuram, fluopyram, flutolanil, fluxapyroxad, furametpyr, isopyrazam, mepronil, oxylcarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide and N-[9-(dichloromethylene)-1,2,3,4-tetrahydro-1,4-methanonaphthalen-5-yl]-3-(difluoromethyl)-1-methyl-1H-pyrazole-4-carboxamide (Hambra/SYN192);

other respiration inhibitors (e.g. complex I, uncouplers): diflumetorim; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI fungicides)
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: imazalil, pefurazoate, prochloraz, triflumizol; pyrimidines, pyridines and piperazines: fenarimol, nuarimol, pyrifenox, triforine;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic acid synthesis inhibitors
phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate;

D) Inhibitors of cell division and cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of amino acid and protein synthesis
methionine synthesis inhibitors (anilino-pyrimidines): cyprodinil, mepanipyrim, pyrimethanil;

protein synthesis inhibitors: blasticidin-S, kasugamycin, kasugamycin hydrochloridehydrate, mildiomycin, streptomycin, oxytetracyclin, polyoxine, validamycin A;

F) Signal transduction inhibitors
  MAP/histidine kinase inhibitors: fluoroimid, iprodione, procymidone, vinclozolin, fenpiclonil, fludioxonil;
  G protein inhibitors: quinoxyfen;
G) Lipid and membrane synthesis inhibitors
  Phospholipid biosynthesis inhibitors: edifenphos, iprobenfos, pyrazophos, isoprothiolane;
  lipid peroxidation: dicloran, quintozene, tecnazene, tolclofos-methyl, biphenyl, chloroneb, etridiazole;
  phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
  compounds affecting cell membrane permeability and fatty acides: propamocarb, propamocarb-hydrochlorid
H) Inhibitors with Multi Site Action
  inorganic active substances: Bordeaux mixture, copper acetate, copper hydroxide, copper oxychloride, basic copper sulfate, sulfur;
  thio- and dithiocarbamates: ferbam, mancozeb, maneb, metam, metiram, propineb, thiram, zineb, ziram;
  organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
  guanidines and others: guanidine, dodine, dodine free base, guazatine, guazatineacetate, iminoctadine, iminoctadine-triacetate, iminoctadine-tris(albesilate), dithianon;
I) Cell wall synthesis inhibitors
  inhibitors of glucan synthesis: validamycin, polyoxin B;
  melanin synthesis inhibitors: pyroquilon, tricyclazole, carpropamid, dicyclomet, fenoxanil;
J) Plant defence inducers
  acibenzolar-5-methyl, probenazole, isotianil, tiadinil, prohexadione-calcium; phosphonates: fosetyl, fosetyl-aluminum, phosphorous acid and its salts;
K) Unknown mode of action
  bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl form amidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide, 3-[5-(4-methylphenyl)-2,3-dimethyl-isoxazolidin-3-yl]pyridine, 3-[5-(4-chlorophenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxyacetamide;
L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLA-GUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amylolique-faciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Clyphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone Biolnnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma Bio-Works Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. vinde* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth regulators
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides
- acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
- amino acid derivatives: bilanafos, glyphosate, glufosinate, sulfosate;
- aryloxyphenoxypropionates: clodinafop, cyhalofop-butyl, fenoxaprop, fluazifop, haloxyfop, metamifop, propaquizafop, quizalofop, quizalofop-P-tefuryl;
- Bipyridyls: diquat, paraquat;
- (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
- cyclohexanediones: butroxydim, clethodim, cycloxydim, profoxydim, sethoxydim, tepraloxydim, tralkoxydim;
- dinitroanilines: benfluralin, ethalfluralin, oryzalin, pendimethalin, prodiamine, trifluralin;
- diphenyl ethers: acifluorfen, aclonifen, bifenox, diclofop, ethoxyfen, fomesafen, lactofen, oxyfluorfen;
- hydroxybenzonitriles: bomoxynil, dichlobenil, ioxynil;
- imidazolinones: imazamethabenz, imazamox, imazapic, imazapyr, imazaquin, imazethapyr;
- phenoxy acetic acids: clomeprop, 2,4-dichlorophenoxy-acetic acid (2,4-D), 2,4-DB, dichlorprop, MCPA, MCPA-thioethyl, MCPB, Mecoprop;
- pyrazines: chloridazon, flufenpyr-ethyl, fluthiacet, norflurazon, pyridate;
- pyridines: aminopyralid, clopyralid, diflufenican, dithiopyr, fluridone, fluoroxypyr, picloram, picolinafen, thiazopyr;
- sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yOurea;
- triazines: ametryn, atrazine, cyanazine, dimethametryn, ethiozin, hexazinone, metamitron, metribuzin, prometryn, simazine, terbuthylazine, terbutryn, triaziflam;
- ureas: chlorotoluron, daimuron, diuron, fluometuron, isoproturon, linuron, methabenzthiazuron, tebuthiuron;
- other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
- others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidonethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides
- organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
- carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
- pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
- insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
- nicotinic receptor agonists/antagonists compounds: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
macrocyclic lactone insecticides: abamectin, emamectin, milbemectin, lepimectin, spinosad, spinetoram;
mitochondrial electron transport inhibitor (METI) I acaricides: fenazaquin, pyridaben, tebufenpyrad, tolfenpyrad, flufenerim;
METI II and III compounds: acequinocyl, fluacyprim, hydramethylnon;
Uncouplers: chlorfenapyr;
oxidative phosphorylation inhibitors: cyhexatin, diafenthiuron, fenbutatin oxide,
propargite;
moulting disruptor compounds: cryomazine;
mixed function oxidase inhibitors: piperonyl butoxide;
sodium channel blockers: indoxacarb, metaflumizone;
others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound I (component 1) and at least one further active substance useful for plant protection, e.g. selected from the groups A) to O) (component 2), in particular one further fungicide, e.g. one or more fungicide from the groups A) to F), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to L), as described above, is more efficient than combating those fungi with individual compounds I or individual fungicides from groups A) to L). By applying compounds I together with at least one active substance from groups A) to O) a synergistic effect can be obtained, i.e. more then simple addition of the individual effects is obtained (synergistic mixtures).

According to this invention, applying the compounds I together with at least one further active substance is to be understood to denote, that at least one compound of formula I and at least one further active substance occur simultaneously at the site of action (i.e. the harmful fungi to be controlled or their habitats such as infected plants, plant propagation materials, particularly seeds, surfaces, materials or the soil as well as plants, plant propagation materials, particularly seeds, soil, surfaces, materials or rooms to be protected from fungal attack) in a fungicidally effective amount. This can be obtained by applying the compounds I and at least one further active substance simultaneously, either jointly (e.g. as tank-mix) or sperately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E.g., kits may include one or more fungicide component(s) and/or an adjuvant component and/or a insecticide component and/or a growth regulator component and/or a herbicde. One or more of the components may already be combined together or preformulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not preformulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual components of the composition according to the invention such as parts of a kit or parts of a binary or ternary mixture may be mixed by the user himself in a spray tank and further auxiliaries may be added, if appropriate (tank mix).

In a further embodiment, either individual components of the composition according to the invention or partially premixed components, e.g. components comprising compounds I and/or active substances from the groups A) to O), may be mixed by the user in a spray tank and further auxiliaries and additives may be added, if appropriate (tank mix).

In a further embodiment, either individual components of the composition according to the invention or partially premixed components, e.g. components comprising compounds I and/or active substances from the groups A) to O), can be applied jointly (e.g. after tankmix) or consecutively.

Preference is also given to mixtures comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I (component 1) and at least one active substance selected from group C) (component 2) and particularly selected from metalaxyl, (metalaxyl-M) mefenoxam, ofurace.

Preference is given to mixtures comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I (component 1) and at least one active substance selected from group E) (component 2) and particularly selected from cyprodinil, mepanipyrim, pyrimethanil.

Preference is also given to mixtures comprising a compound I (component 1) and at least one active substance selected from group F) (component 2) and particularly selected from iprodione, fludioxonil, vinclozolin, quinoxyfen.

Preference is also given to mixtures comprising a compound I (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I (component 1) and at least one active substance selected from group I) (component 2) and particularly selected from carpropamid and fenoxanil.

Preference is also given to mixtures comprising a compound I (component 1) and at least one active substance selected from group J) (component 2) and particularly selected from acibenzolar-5-methyl, probenazole, tiadinil, fosetyl, fosetyl-aluminium, $H_3PO_3$ and salts thereof.

Preference is also given to mixtures comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprising a compound I (component 1) and at least one active substance selected from group L) (component 2) and particularly selected from *Bacillus subtilis* strain NRRL No. B-21661, *Bacillus pumilus* strain NRRL No. B-30087 and *Ulocladium oudemansii*.

Accordingly, the present invention furthermore relates to compositions comprising one compound I (component 1) and one further active substance (component 2), which further active substance is selected from the column "Component 2" of the lines B-1 to B-351 of Table B.

A further embodiment relates to the compositions B-1 to B-351 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indiviualized compound I and one further active substance from groups A) to O)

| Mixture | Component 1 | Component 2 |
| --- | --- | --- |
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |

TABLE B-continued

Composition comprising one indiviualized compound I and one further active substance from groups A) to O)

| Mixture | Component 1 | Component 2 |
|---|---|---|
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Bixafen |
| B-25 | one individualized compound I | Boscalid |
| B-26 | one individualized compound I | Carboxin |
| B-27 | one individualized compound I | Fenfuram |
| B-28 | one individualized compound I | Fenhexamid |
| B-29 | one individualized compound I | Flutolanil |
| B-30 | one individualized compound I | Fluxapyroxad |
| B-31 | one individualized compound I | Furametpyr |
| B-32 | one individualized compound I | Isopyrazam |
| B-33 | one individualized compound I | Isotianil |
| B-34 | one individualized compound I | Kiralaxyl |
| B-35 | one individualized compound I | Mepronil |
| B-36 | one individualized compound I | Metalaxyl |
| B-37 | one individualized compound I | Metalaxyl-M |
| B-38 | one individualized compound I | Ofurace |
| B-39 | one individualized compound I | Oxadixyl |
| B-40 | one individualized compound I | Oxycarboxin |
| B-41 | one individualized compound I | Penflufen |
| B-42 | one individualized compound I | Penthiopyrad |
| B-43 | one individualized compound I | Sedaxane |
| B-44 | one individualized compound I | Tecloftalam |
| B-45 | one individualized compound I | Thifluzamide |
| B-46 | one individualized compound I | Tiadinil |
| B-47 | one individualized compound I | 2-Amino-4-methyl-thiazole-5-carboxylic acid anilide |
| B-48 | one individualized compound I | N-(4'-trifluoromethylthiobiphenyl-2-yl)-3-difluoromethyl-1-methyl-1H-pyrazole-4-carboxamide |
| B-49 | one individualized compound I | N-(2-(1,3,3-trimethyl-butyl)-phenyl)-1,3-dimethyl-5-fluoro-1H-pyrazole-4-carboxamide |
| B-50 | one individualized compound I | N-[9-(dichloromethylene)-1,2,3,4-tetrahydro-1,4-methanonaphthalen-5-yl]-3-(difluoromethyl)-1-methyl-1H-pyrazole-4-carboxamide |
| B-51 | one individualized compound I | Dimethomorph |
| B-52 | one individualized compound I | Flumorph |
| B-53 | one individualized compound I | Pyrimorph |
| B-54 | one individualized compound I | Flumetover |
| B-55 | one individualized compound I | Fluopicolide |
| B-56 | one individualized compound I | Fluopyram |
| B-57 | one individualized compound I | Zoxamide |
| B-58 | one individualized compound I | Carpropamid |
| B-59 | one individualized compound I | Diclocymet |
| B-60 | one individualized compound I | Mandipropamid |
| B-61 | one individualized compound I | Oxytetracyclin |
| B-62 | one individualized compound I | Silthiofam |
| B-63 | one individualized compound I | N-(6-methoxy-pyridin-3-yl) cyclopropanecarboxylic acid amide |
| B-64 | one individualized compound I | Azaconazole |
| B-65 | one individualized compound I | Bitertanol |
| B-66 | one individualized compound I | Bromuconazole |
| B-67 | one individualized compound I | Cyproconazole |
| B-68 | one individualized compound I | Difenoconazole |
| B-69 | one individualized compound I | Diniconazole |
| B-70 | one individualized compound I | Diniconazole-M |
| B-71 | one individualized compound I | Epoxiconazole |
| B-72 | one individualized compound I | Fenbuconazole |
| B-73 | one individualized compound I | Fluquinconazole |
| B-74 | one individualized compound I | Flusilazole |
| B-75 | one individualized compound I | Flutriafol |
| B-76 | one individualized compound I | Hexaconazol |
| B-77 | one individualized compound I | Imibenconazole |
| B-78 | one individualized compound I | Ipconazole |
| B-79 | one individualized compound I | Metconazole |
| B-80 | one individualized compound I | Myclobutanil |

TABLE B-continued

Composition comprising one indiviualized compound I and one further active substance from groups A) to O)

| Mixture | Component 1 | Component 2 |
|---|---|---|
| B-81 | one individualized compound I | Oxpoconazol |
| B-82 | one individualized compound I | Paclobutrazol |
| B-83 | one individualized compound I | Penconazole |
| B-84 | one individualized compound I | Propiconazole |
| B-85 | one individualized compound I | Prothioconazole |
| B-86 | one individualized compound I | Simeconazole |
| B-87 | one individualized compound I | Tebuconazole |
| B-88 | one individualized compound I | Tetraconazole |
| B-89 | one individualized compound I | Triadimefon |
| B-90 | one individualized compound I | Triadimenol |
| B-91 | one individualized compound I | Triticonazole |
| B-92 | one individualized compound I | Uniconazole |
| B-93 | one individualized compound I | Cyazofamid |
| B-94 | one individualized compound I | Imazalil |
| B-95 | one individualized compound I | Imazalil-sulfate |
| B-96 | one individualized compound I | Pefurazoate |
| B-97 | one individualized compound I | Prochloraz |
| B-98 | one individualized compound I | Triflumizole |
| B-99 | one individualized compound I | Benomyl |
| B-100 | one individualized compound I | Carbendazim |
| B-101 | one individualized compound I | Fuberidazole |
| B-102 | one individualized compound I | Thiabendazole |
| B-103 | one individualized compound I | Ethaboxam |
| B-104 | one individualized compound I | Etridiazole |
| B-105 | one individualized compound I | Hymexazole |
| B-106 | one individualized compound I | 2-(4-Chloro-phenyl)-N-[4-(3,4-dimethoxy-phenyl)-isoxazol-5-yl]-2-prop-2-ynyloxy-acetamide |
| B-107 | one individualized compound I | Fluazinam |
| B-108 | one individualized compound I | Pyrifenox |
| B-109 | one individualized compound I | 3-[5-(4-Chloro-phenyl)-2,3-dimethyl-isoxazolidin-3-yl]pyridine (Pyrisoxazole) |
| B-110 | one individualized compound I | 3-[5-(4-Methyl-phenyl)-2,3-dimethyl-isoxazolidin-3-yl]-pyridine |
| B-111 | one individualized compound I | Bupirimate |
| B-112 | one individualized compound I | Cyprodinil |
| B-113 | one individualized compound I | Diflumetorim |
| B-114 | one individualized compound I | Fenarimol |
| B-115 | one individualized compound I | Ferimzone |
| B-116 | one individualized compound I | Mepanipyrim |
| B-117 | one individualized compound I | Nitrapyrin |
| B-118 | one individualized compound I | Nuarimol |
| B-119 | one individualized compound I | Pyrimethanil |
| B-120 | one individualized compound I | Triforine |
| B-121 | one individualized compound I | Fenpiclonil |
| B-122 | one individualized compound I | Fludioxonil |
| B-123 | one individualized compound I | Aldimorph |
| B-124 | one individualized compound I | Dodemorph |
| B-125 | one individualized compound I | Dodemorph-acetate |
| B-126 | one individualized compound I | Fenpropimorph |
| B-127 | one individualized compound I | Tridemorph |
| B-128 | one individualized compound I | Fenpropidin |
| B-129 | one individualized compound I | Fluoroimid |
| B-130 | one individualized compound I | Iprodione |
| B-131 | one individualized compound I | Procymidone |
| B-132 | one individualized compound I | Vinclozolin |
| B-133 | one individualized compound I | Famoxadone |
| B-134 | one individualized compound I | Fenamidone |
| B-135 | one individualized compound I | Flutianil |
| B-136 | one individualized compound I | Octhilinone |
| B-137 | one individualized compound I | Probenazole |
| B-138 | one individualized compound I | Fenpyrazamine |
| B-139 | one individualized compound I | Acibenzolar-S-methyl |
| B-140 | one individualized compound I | Ametoctradin |
| B-141 | one individualized compound I | Amisulbrom |
| B-142 | one individualized compound I | Anilazin |
| B-143 | one individualized compound I | Blasticidin-S |
| B-144 | one individualized compound I | Captafol |
| B-145 | one individualized compound I | Captan |
| B-146 | one individualized compound I | Chinomethionat |
| B-147 | one individualized compound I | Dazomet |
| B-148 | one individualized compound I | Debacarb |
| B-149 | one individualized compound I | Diclomezine |
| B-150 | one individualized compound I | Difenzoquat, |
| B-151 | one individualized compound I | Difenzoquat-methylsulfate |

TABLE B-continued

Composition comprising one indiviualized compound I and one further active substance from groups A) to O)

| Mixture | Component 1 | Component 2 |
|---|---|---|
| B-152 | one individualized compound I | Fenoxanil |
| B-153 | one individualized compound I | Folpet |
| B-154 | one individualized compound I | Oxolinsäure |
| B-155 | one individualized compound I | Piperalin |
| B-156 | one individualized compound I | Proquinazid |
| B-157 | one individualized compound I | Pyroquilon |
| B-158 | one individualized compound I | Quinoxyfen |
| B-159 | one individualized compound I | Triazoxid |
| B-160 | one individualized compound I | Tricyclazole |
| B-161 | one individualized compound I | 2-Butoxy-6-iodo-3-propyl-chromen-4-one |
| B-162 | one individualized compound I | 5-Chloro-1-(4,6-dimethoxy-pyrimidin-2-yl)-2-methyl-1H-benzoimidazole |
| B-163 | one individualized compound I | 5-Chloro-7-(4-methyl-piperidin-1-yl)-6-(2,4,6-trifluoro-phenyl)-[1,2,4]triazolo[1,5-a]pyrimidine |
| B-164 | one individualized compound I | Ferbam |
| B-165 | one individualized compound I | Mancozeb |
| B-166 | one individualized compound I | Maneb |
| B-167 | one individualized compound I | Metam |
| B-168 | one individualized compound I | Methasulphocarb |
| B-169 | one individualized compound I | Metiram |
| B-170 | one individualized compound I | Propineb |
| B-171 | one individualized compound I | Thiram |
| B-172 | one individualized compound I | Zineb |
| B-173 | one individualized compound I | Ziram |
| B-174 | one individualized compound I | Diethofencarb |
| B-175 | one individualized compound I | Benthiavalicarb |
| B-176 | one individualized compound I | Iprovalicarb |
| B-177 | one individualized compound I | Propamocarb |
| B-178 | one individualized compound I | Propamocarb hydrochlorid |
| B-179 | one individualized compound I | Valifenalate |
| B-180 | one individualized compound I | N-(1-(1-(4-cyanophenyl)ethanesulfonyl)-but-2-yl) carbamic acid-(4-fluoro-phenyl) ester |
| B-181 | one individualized compound I | Dodine |
| B-182 | one individualized compound I | Dodine free base |
| B-183 | one individualized compound I | Guazatine |
| B-184 | one individualized compound I | Guazatine-acetate |
| B-185 | one individualized compound I | Iminoctadine |
| B-186 | one individualized compound I | Iminoctadine-triacetate |
| B-187 | one individualized compound I | Iminoctadine-tris(albesilate) |
| B-188 | one individualized compound I | Kasugamycin |
| B-189 | one individualized compound I | Kasugamycin-hydrochloride-hydrate |
| B-190 | one individualized compound I | Polyoxine |
| B-191 | one individualized compound I | Streptomycin |
| B-192 | one individualized compound I | Validamycin A |
| B-193 | one individualized compound I | Binapacryl |
| B-194 | one individualized compound I | Dicloran |
| B-195 | one individualized compound I | Dinobuton |
| B-196 | one individualized compound I | Dinocap |
| B-197 | one individualized compound I | Nitrothal-isopropyl |
| B-198 | one individualized compound I | Tecnazen |
| B-199 | one individualized compound I | Fentin salts |
| B-200 | one individualized compound I | Dithianon |
| B-201 | one individualized compound I | Isoprothiolane |
| B-202 | one individualized compound I | Edifenphos |
| B-203 | one individualized compound I | Fosetyl, Fosetyl-aluminium |
| B-204 | one individualized compound I | Iprobenfos |
| B-205 | one individualized compound I | Phosphorous acid ($H_3PO_3$) and derivatives |
| B-206 | one individualized compound I | Pyrazophos |
| B-207 | one individualized compound I | Tolclofos-methyl |
| B-208 | one individualized compound I | Chlorothalonil |
| B-209 | one individualized compound I | Dichlofluanid |
| B-210 | one individualized compound I | Dichlorophen |
| B-211 | one individualized compound I | Flusulfamide |
| B-212 | one individualized compound I | Hexachlorbenzene |
| B-213 | one individualized compound I | Pencycuron |
| B-214 | one individualized compound I | Pentachlorophenol and salts |
| B-215 | one individualized compound I | Phthalide |
| B-216 | one individualized compound I | Quintozene |
| B-217 | one individualized compound I | Thiophanate Methyl |
| B-218 | one individualized compound I | Tolylfluanid |
| B-219 | one individualized compound I | N-(4-chloro-2-nitro-phenyl)-N-ethyl-4-methyl-benzenesulfonamide |

TABLE B-continued

Composition comprising one indiviualized compound I and one further active substance from groups A) to O)

| Mixture | Component 1 | Component 2 |
|---|---|---|
| B-220 | one individualized compound I | Bordeaux mixture |
| B-221 | one individualized compound I | Copper acetate |
| B-222 | one individualized compound I | Copper hydroxide |
| B-223 | one individualized compound I | Copper oxychloride |
| B-224 | one individualized compound I | basic Copper sulfate |
| B-225 | one individualized compound I | Sulfur |
| B-226 | one individualized compound I | Biphenyl |
| B-227 | one individualized compound I | Bronopol |
| B-228 | one individualized compound I | Cyflufenamid |
| B-229 | one individualized compound I | Cymoxanil |
| B-230 | one individualized compound I | Diphenylamin |
| B-231 | one individualized compound I | Metrafenone |
| B-232 | one individualized compound I | Pyriofenone |
| B-233 | one individualized compound I | Mildiomycin |
| B-234 | one individualized compound I | Oxin-copper |
| B-235 | one individualized compound I | Prohexadione calcium |
| B-236 | one individualized compound I | Spiroxamine |
| B-237 | one individualized compound I | Tebufloquin |
| B-238 | one individualized compound I | Tolylfluanid |
| B-239 | one individualized compound I | N-(Cyclopropylmethoxyimino-(6-difluoromethoxy-2,3-difluoro-phenyl)-methyl)-2-phenyl acetamide |
| B-240 | one individualized compound I | N'-(4-(4-chloro-3-trifluoromethyl-phenoxy)-2,5-dimethyl-phenyl)-N-ethyl-N-methyl formamidine |
| B-241 | one individualized compound I | N'-(4-(4-fluoro-3-trifluoromethyl-phenoxy)-2,5-dimethyl-phenyl)-N-ethyl-N-methyl formamidine |
| B-242 | one individualized compound I | N'-(2-methyl-5-trifluoromethy1-4-(3-tri-methylsilanyl-propoxy)-phenyl)-N-ethyl-N-methyl formamidine |
| B-243 | one individualized compound I | N'-(5-difluoromethy1-2-methyl-4-(3-tri-methylsilanyl-propoxy)-phenyl)-N-ethyl-N-methyl formamidine |
| B-244 | one individualized compound I | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-245 | one individualized compound I | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-246 | one individualized compound I | 1-[4-[4-[5-(2,6-difluorophenyl)-4,5-di-hydro-3-isoxazolyl]-2-thiazolyl]-1-pi-peridinyl]-2-[5-methyl-3-(trifluoro-methyl)-1H-pyrazol-1-yl]ethanone |
| B-247 | one individualized compound I | Methoxy-acetic acid 6-tert-butyl-8-fluoro-2,3-dimethyl-quinolin-4-yl ester |
| B-248 | one individualized compound I | N-Methyl-2-{1-[(5-methyl-3-trifluoro-methyl-1H-pyrazol-1-yl)-acetyl]-piperi-din-4-yl}-N-[(1R)-1,2,3,4-tetrahydro-naphthalen-1-yl]-4-thiazolecarboxamide |
| B-249 | one individualized compound I | *Bacillus subtilis* NRRL No. B-21661 |
| B-250 | one individualized compound I | *Bacillus pumilus* NRRL No. B-30087 |
| B-251 | one individualized compound I | *Ulocladium oudemansii* |
| B-252 | one individualized compound I | Carbaryl |
| B-253 | one individualized compound I | Carbofuran |
| B-254 | one individualized compound I | Carbosulfan |
| B-255 | one individualized compound I | Methomylthiodicarb |
| B-256 | one individualized compound I | Bifenthrin |
| B-257 | one individualized compound I | Cyfluthrin |
| B-258 | one individualized compound I | Cypermethrin |
| B-259 | one individualized compound I | alpha-Cypermethrin |
| B-260 | one individualized compound I | zeta-Cypermethrin |
| B-261 | one individualized compound I | Deltamethrin |
| B-262 | one individualized compound I | Esfenvalerate |
| B-263 | one individualized compound I | Lambda-cyhalothrin |
| B-264 | one individualized compound I | Permethrin |
| B-265 | one individualized compound I | Tefluthrin |
| B-266 | one individualized compound I | Diflubenzuron |
| B-267 | one individualized compound I | Flufenoxuron |
| B-268 | one individualized compound I | Lufenuron |
| B-269 | one individualized compound I | Teflubenzuron |

TABLE B-continued

Composition comprising one indiviualized compound I and one further active substance from groups A) to O)

| Mixture | Component 1 | Component 2 |
|---|---|---|
| B-270 | one individualized compound I | Spirotetramate |
| B-271 | one individualized compound I | Clothianidin |
| B-272 | one individualized compound I | Dinotefuran |
| B-273 | one individualized compound I | Imidacloprid |
| B-274 | one individualized compound I | Thiamethoxam |
| B-275 | one individualized compound I | Acetamiprid |
| B-276 | one individualized compound I | Thiacloprid |
| B-277 | one individualized compound I | Endosulfan |
| B-278 | one individualized compound I | Fipronil |
| B-279 | one individualized compound I | Abamectin |
| B-280 | one individualized compound I | Emamectin |
| B-281 | one individualized compound I | Spinosad |
| B-282 | one individualized compound I | Spinetoram |
| B-283 | one individualized compound I | Hydramethylnon |
| B-284 | one individualized compound I | Chlorfenapyr |
| B-285 | one individualized compound I | Fenbutatin oxide |
| B-286 | one individualized compound I | Indoxacarb |
| B-287 | one individualized compound I | Metaflumizone |
| B-288 | one individualized compound I | Flonicamid |
| B-289 | one individualized compound I | Lubendiamide |
| B-290 | one individualized compound I | Chlorantraniliprole |
| B-291 | one individualized compound I | Cyazypyr (HGW86) |
| B-292 | one individualized compound I | Cyflumetofen |
| B-293 | one individualized compound I | Acetochlor |
| B-294 | one individualized compound I | Dimethenamid |
| B-295 | one individualized compound I | metolachlor |
| B-296 | one individualized compound I | Metazachlor |
| B-297 | one individualized compound I | Glyphosate |
| B-298 | one individualized compound I | Glufosinate |
| B-299 | one individualized compound I | Sulfosate |
| B-300 | one individualized compound I | Clodinafop |
| B-301 | one individualized compound I | Fenoxaprop |
| B-302 | one individualized compound I | Fluazifop |
| B-303 | one individualized compound I | Haloxyfop |
| B-304 | one individualized compound I | Paraquat |
| B-305 | one individualized compound I | Phenmedipham |
| B-306 | one individualized compound I | Clethodim |
| B-307 | one individualized compound I | Cycloxydim |
| B-308 | one individualized compound I | Profoxydim |
| B-309 | one individualized compound I | Sethoxydim |
| B-310 | one individualized compound I | Tepraloxydim |
| B-311 | one individualized compound I | Pendimethalin |
| B-312 | one individualized compound I | Prodiamine |
| B-313 | one individualized compound I | Trifluralin |
| B-314 | one individualized compound I | Acifluorfen |
| B-315 | one individualized compound I | Bromoxynil |
| B-316 | one individualized compound I | Imazamethabenz |
| B-317 | one individualized compound I | Imazamox |
| B-318 | one individualized compound I | Imazapic |
| B-319 | one individualized compound I | Imazapyr |
| B-320 | one individualized compound I | Imazaquin |
| B-321 | one individualized compound I | Imazethapyr |
| B-322 | one individualized compound I | 2,4-Dichlorophenoxyacetic acid (2,4-D) |
| B-323 | one individualized compound I | Chloridazon |
| B-324 | one individualized compound I | Clopyralid |
| B-325 | one individualized compound I | Fluroxypyr |
| B-326 | one individualized compound I | Picloram |
| B-327 | one individualized compound I | Picolinafen |
| B-328 | one individualized compound I | Bensulfuron |
| B-329 | one individualized compound I | Chlorimuron-ethyl |
| B-330 | one individualized compound I | Cyclosulfamuron |
| B-331 | one individualized compound I | Iodosulfuron |
| B-332 | one individualized compound I | Mesosulfuron |
| B-333 | one individualized compound I | Metsulfuron-methyl |
| B-334 | one individualized compound I | Nicosulfuron |
| B-335 | one individualized compound I | Rimsulfuron |
| B-336 | one individualized compound I | Triflusulfuron |
| B-337 | one individualized compound I | Atrazine |
| B-338 | one individualized compound I | Hexazinone |
| B-339 | one individualized compound I | Diuron |
| B-340 | one individualized compound I | Florasulam |
| B-341 | one individualized compound I | Pyroxasulfone |
| B-342 | one individualized compound I | Bentazone |
| B-343 | one individualized compound I | Cinidon-ethyl |
| B-344 | one individualized compound I | Cinmethylin |

TABLE B-continued

Composition comprising one indiviualized compound I and one further active substance from groups A) to O)

| Mixture | Component 1 | Component 2 |
|---|---|---|
| B-345 | one individualized compound I | Dicamba |
| B-346 | one individualized compound I | Diflufenzopyr |
| B-347 | one individualized compound I | Quinclorac |
| B-348 | one individualized compound I | Quinmerac |
| B-349 | one individualized compound I | Mesotrione |
| B-350 | one individualized compound I | Saflufenacil |
| B-351 | one individualized compound I | Topramezone |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

The mixtures of active substances can be prepared as compositions comprising besides the active ingridients at least one inert ingredient by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

SYNTHESIS EXAMPLES

With due modification of the starting compounds, the procedures shown in the synthesis examples below were used to obtain further compounds I. The resulting compounds, together with physical data, are listed in Table I below.

Ex. 1

2,6-Diallyl-1H,5H-[1,4]dithiino[2,3-c:5,6-c']dipyrrol-1,3,5,7(2H,6H)tetrone (I-1)

0.13 g (0.51 mmol) 1.4-Dithiin-tetracarboxylic acid-dianhydride (see Chem. Ber. 100. (1967) 1559) and 0.1 g (1.75 mmol) allylamine in 2 ml acetic acid were stirred at about 60° C. After 3 hours the solvent was evaporated and the residue was purified via preparative MPLC over RP 18 silica with an acetonitrile/water gradient. 20 mg (11% of theory) of the title compound were obtained as a greenish solid (m.p. 258° C.).

$^1$H-NMR (dmso-$d_6$. δ in ppm): 5.75 (m. 1H); 5.15 (m. 2H); 4.4 (s. broad. 2H).

Ex. 2

2,6-Dipropargyl-1H,5H-[1,4]dithiino[2,3-c:5,6-c']dipyrrol-1,3,5,7(2H,6H)tetrone (I-14)

Step 1 Preparation of 4-Oxo-4-(prop-2-ynylamino)butanoic acid 1.6 g (16 mmol) Succinic anhydride and 1.06 g (19.2 mmol) propargylamine in 10 ml tetrahydrofuran were stirred over night at room temperature whereat a solid precipitated. The reaction mixture was taken up with methyl-t-butyl ether (MTBE) and the insoluble crystals were filtered off and dried in a stream of nitrogen. 2 g (80% of theory) of the title compound were obtained which were used in the next reaction without further purification.

Step 2: Preparation of compound I-14

22 g (185 mmol) Thionylchloride were added dropwise at about 15° C. to a mixture of 3 g (19.3 mmol) 4-oxo-4-(prop-2-ynylamino)butanoic acid (see step 1) in 75 ml dioxane. The reaction mixture was stirred 36 hours at room temperature. Subsequently all volatiles were evaporated under reduced pressure and the residue was stirred with a dichloromethane and water mixture. Afterwards the remaining solid was filtered off. washed with MTBE and dried in a stream of nitrogen. 0.65 g (20% of theory) of the title compound were obtained as a greenish solid.

$^1$H-NMR (DMSO-$d_6$. δ in ppm): 4.2 (s. 2H); 3.4 (s. 1H).

Example 3

2.6-Dimethoxy-1H.5H-[1.4]dithiino[2,3-c:5.6-c']dipyrrol-1.3.5.7(2H.6H)tetrone (I-2)

Step 1: Preparation of 3.4-dichloro-1-methoxy-pyrrole-2.5-dione

At room temperature 3.6 g (52.9 mmol) sodium ethanolate were added to a mixture of 5.6 g (33.5 mmol) 2.3-dichloro maleic anhydride and 4.6 g (55.1 mmol) methoxyamine hydrochloride in 50 ml of acetic acid. The reaction mixture was stirred 16 hours at room temperature and then poured into an ice/water mixture. An insoluble solid crystallized out which was filtered off and washed with water. Then this solid was redissolved in ethyl acetate. the solution was dried over magnesium sulfate and evaporated. 4.5 g (68% of theory) of the title compound were obtained as a light colored solid.

$^1$H-NMR (CDCl$_3$. δ in ppm): 4.0 (s. 3H).

Step 2: Preparation of compound I-2

A hot solution (50-70° C.) of 1 g (5.1 mmol) 3.4-dichloro-1-methoxy-pyrrole-2.5-dione (example 3.1.) in 7.5 ml ethanol was added to a 80° C. hot solution of 1.27 g (5.1 mmol) sodium dithiosulfatex5H$_2$O and the reaction mixture was stirred at about 80° C. for about 30 min. A green precipitate was observed. Afterwards the reaction mixture was allowed to cool to room temperature and water was added. The green precipitate was filtered off, washed with methanol and MTBE and dried in a stream of nitrogen. 0.5 g (62% of theory) of the title compound were obtained as a green solid (mp 295° C.).

$^{13}$C-NMR (dmso-$d_6$; δ in ppm): 159.5; 128.0; 65.7.

TABLE I

Compounds of the formula I.A1.

| ex. no | $R^1$ | $R^2$ | *Phys. Data: m.p. (° C.); $^1$H-NMR (δ in ppm); $^{13}$C-NMR (δ in ppm); MS (EI) |
|---|---|---|---|
| I-1 | —CH$_2$—CH=CH$_2$ | —CH$_2$—CH=CH$_2$ | m.p. 258 |
| I-2 | —OCH$_3$ | —OCH$_3$ | m.p. 295.5 |
| I-3 | —OCH$_2$CH$_3$ | —OCH$_2$CH$_3$ | 196 |
| I-4 | —OCH$_2$CH$_2$CH$_3$ | —OCH$_2$CH$_2$CH$_3$ | m.p. 224.5 |
| I-5 | —CH$_2$CH$_2$CN | —CH$_2$CH$_2$CN | m.p. 325 |
| I-6 | —CH$_2$C(=O)N(CH$_3$)$_2$ | —CH$_2$C(=O)N(CH$_3$)$_2$ | 13C in DMF-$_{d7}$: 165.7; 165.0; 132.0; 40.8; 36.0 |
| I-7 | —CH$_2$CN | —CH$_2$CN | m.p. 291 |
| I-8 | —NH—C(=O)OC(CH$_3$)$_3$ | —NH—C(=O)OC(CH$_3$)$_3$ | 13C in CDCl$_3$: 161.3; 152.8; 131.0; 84.0; 28.0 |
| I-9 | —OC(CH$_3$)$_3$ | —OC(CH$_3$)$_3$ | m.p. 234 |
| I-10 | —CH$_2$CH$_2$N(CH$_3$)$_2$ | —CH$_2$CH$_2$N(CH$_3$)$_2$ | MS: 396 |
| I-11 | —CH$_2$CH$_2$—CH=CH$_2$ | —CH$_2$CH$_2$—CH=CH$_2$ | m.p. 255.5 |
| I-12 | —CH$_2$CH$_2$—C≡CH | —CH$_2$CH$_2$—C≡CH | 1H in DMF-d$_7$: 3.7 (2H); 2.85 (1H); 2.5 (2H) |
| I-13 | —N(CH$_3$)$_2$ | —N(CH$_3$)$_2$ | m.p. 291.5 |
| I-14 | —CH$_2$—C≡CH | —CH$_2$—C≡CH | 1H in DMSO-d$_6$: 4.2 (d); 3.3 (1H) |
| I-15 | —CH$_2$C(=O)NH$_2$ | —CH$_2$C(=O)NH$_2$ | 13C in DMF-d$_7$: 168.7; 165.2; 132.3; 41.8 |
| I-16 | —CH(CH$_3$)CN | —CH(CH$_3$)CN | m.p. 293 |

*Physico-chemical data:
m.p. = melting point (° C.);
1H = $^1$H-NMR (δ in ppm);
$^{13}$C = 13C-NMR (δ in ppm);
MS = mass spectrometry (EI).

II. Examples of the Action Against Harmful Fungi

The fungicidal action of the compounds of the formula I was demonstrated by the following experiments:

A) Microtiter Tests

The active substances were formulated separately as a stock solution in dimethyl sulfoxide (DMSO) at a concentration of 10,000 ppm.

The stock solutions were mixed according to the ratio, pipetted onto a micro titer plate (MTP) and diluted with water to the stated concentrations. A spore suspension of the respective pathogen as indicated in the use examples below in an specific medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

Use Example 1

Activity Against Rice Blast *Pyricularia pryzae*

A spore suspension of *Pyricularia oryzae* in an aqueous biomalt or yeast-bactopeptone-glycerine solution was used.

In this test, the samples which had been treated with 31 ppm of the active substance from examples I-2, I-3, I-4, I-9 and I-11, respectively, showed up to at most 15% growth of the pathogen.

Use Example 2

Activity Against the Late Blight Pathogen *Phytophthora infestans*

A spore suspension of *Phytophtora infestans* containing a pea juice-based aqueous nutrient medium or DDC medium was used.

In this test, the samples which had been treated with 31 ppm of the active substance from examples I-1, I-5, I-6, I-7, I-8, I-10 and I-11 showed up to at most 15% growth of the pathogen.

Use Example 3

Activity Against Leaf Blotch Pathogen *Septoria tritici*

A spore suspension of *Septoria tritici* in an aqueous biomalt or yeast-bactopeptone-glycerine solution was used.

In this test, the samples which had been treated with 31 ppm of the active substance from examples I-1, I-2, I-3, I-4, I-7 and I-12, respectively, showed up to at most 15% growth of the pathogen.

III. Comparative Examples

The spray solutions were prepared in several steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml.

This stock solution was diluted with the described solvent-emulsifier-water mixture to the given concentration.

Use Example 4

Control of Brown Rust on Wheat Caused by *Puccinia recondita*

The first two developed leaves of pot-grown wheat seedling were sprayed to run-off with an aqueous suspension, containing 500 ppm of active ingredient as described below. The next day the plants were inoculated with spores of *Puccinia recondita*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20-24° C. and a relative humidity between 65 and 70%. The extent of fungal attack on the leaves was visually assessed as % diseased leaf area.

| Compound no. | Chemical structure | Disease level (%) |
|---|---|---|
| No. 1 according to prior art WO 2010/043319, Table 1, page 28 | [structure] | 80 |
| No. I-2 according to present invention | [structure] | 45 |
| Untreated control | | 90 |

The invention claimed is:

1. A method for combating harmful fungi, comprising: treating the fungi or the materials, plants, the soil or seeds to be protected against fungal attack with an effective amount of at least one compound of formula I

[structure I]

wherein:
X is O;
k is zero;
$R^1$ is $C_2$-$C_6$-alkenyl or $C_2$-$C_6$-alkynyl,
$R^2$ is $C_2$-$C_6$-alkenyl or $C_2$-$C_6$-alkynyl;
or the N-oxide or the agriculturally acceptable salt thereof.

2. The method of claim 1, wherein $R^2$ is identical to $R^1$.

3. Seed coated with at least one compound of formula I,

[structure I]

wherein:
X is O;
k is 0;
$R^1$ is $C_2$-$C_6$-alkenyl or $C_2$-$C_6$-alkynyl,
$R^2$ is $C_2$-$C_6$-alkenyl or $C_2$-$C_6$-alkynyl;
or an N-oxide or an agriculturally acceptable salt thereof, in an amount of from 0.1 g to 10 kg per 100 kg of seed.

4. A compound of formula I

[structure I]

wherein:
X is O;
k is zero;
$R^1$ is $C_2$-$C_6$-alkenyl or $C_2$-$C_6$-alkynyl,
$R^2$ is $C_2$-$C_6$-alkenyl or $C_2$-$C_6$-alkynyl,
except for 2,6-diallyl[1,4]dithiino[2,3-c;5,6-c']dipyrrole-1,3,5,7-tetraone;
and an N-oxide or an agriculturally acceptable salt thereof.

5. The compound of claim 4, wherein $R^2$ is identical to $R^1$.

6. Compounds of formula V

[structure V]

wherein
$R^1$ is $C_2$-$C_6$-alkenyl or $C_2$-$C_6$-alkynyl,
$R^2$ is $C_2$-$C_6$-alkenyl or $C_2$-$C_6$-alkynyl;
except 3,7-bis-[(Z)-allylimino]-3H,7H-[1,4]dithiino[2,3-c;5,6-c']difuran-1,5-dione.

7. An agrochemical composition wherein said composition comprises a solvent or solid carrier and at least one compound of formula I, as defined in claim 4.

8. The composition according to claim 7, comprising additionally a further active compound.

* * * * *